United States Patent [19]

Waxman et al.

[11] 4,231,373
[45] Nov. 4, 1980

[54] ULTRASONIC IMAGING APPARATUS

[75] Inventors: Albert S. Waxman, Los Gatos; James F. Havlice, Los Altos, both of Calif.

[73] Assignee: Diasonics, Sunnyvale, Calif.

[21] Appl. No.: 925,701

[22] Filed: Jul. 18, 1978

[51] Int. Cl.³ .............................................. A61B 10/00
[52] U.S. Cl. .................................... 128/660; 73/621
[58] Field of Search ........... 310/8 MM; 128/660–663; 73/644, 618–626; 367/104–105, 119–121

[56] References Cited

U.S. PATENT DOCUMENTS

| | | | |
|---|---|---|---|
| 4,047,520 | 9/1977 | Soldner et al. | 73/620 |
| 4,094,306 | 6/1978 | Kossoff | 73/620 |
| 4,103,677 | 8/1978 | Lansiart et al. | 73/621 |
| 4,137,777 | 2/1979 | Haverl et al. | 73/620 |
| 4,143,554 | 3/1979 | Nagy et al. | 73/642 |
| 4,149,419 | 4/1979 | Connell, Jr. et al. | 73/621 |

FOREIGN PATENT DOCUMENTS

| | | | |
|---|---|---|---|
| 546338 | 7/1942 | United Kingdom. | |
| 1490412 | 11/1977 | United Kingdom | 73/620 |

OTHER PUBLICATIONS

Dick, D. E. et al., "High Resolution Rotating Head UTS Scanner" PCT/US79/00487 Int. Pub. 2/7/80, Int. Pri. 7/5/79 Priority 7/5/78.
Krautknawer, *Ultrasonic Testing of Materials*, 2nd Edition, Springer Publ. Co. 1977, pp. 23–27, 222–223, 232, 233–235.
Holm, H. H. et al., "A New Mechanical Real-Time UTS Contact Scanner", *Ultrasound in Med. & Biol.*, Oct. 1975, vol. 2, No. 1 pp. 19–23.
Kossoff, G. et al., "Octoson: A New Rapid Multi-Transducer General Purpose Water-Coupling Echoscope", *Proc. of the 2nd Europ. Cong. on UTS in Medicine*, Munich, Germany, May 12–16, 1975, p. 90–95.

*Primary Examiner*—Robert W. Michell
*Assistant Examiner*—Francis J. Jaworski
*Attorney, Agent, or Firm*—Blakely, Sokoloff, Taylor & Zafman

[57] ABSTRACT

A data acquisition head for an ultrasonic imaging system which employs a plurality of transducers is disclosed. The transducers are rotated in a liquid filled chamber at a constant rate, each about an axis perpendicular to its transmission axis. The transducers are sequentially activated as their transmission axes cross a semi-rigid membrane which is in contact with the body. The acoustic impedance of the liquid and membrane, and the thickness of the membrane, are matched to enhance transmission. In one embodiment, the membrane is one-half or a full wavelength thick and comprises a low density polyethylene and the liquid has an acoustic impedance approximately equal to that of the polyethylene.

6 Claims, 11 Drawing Figures

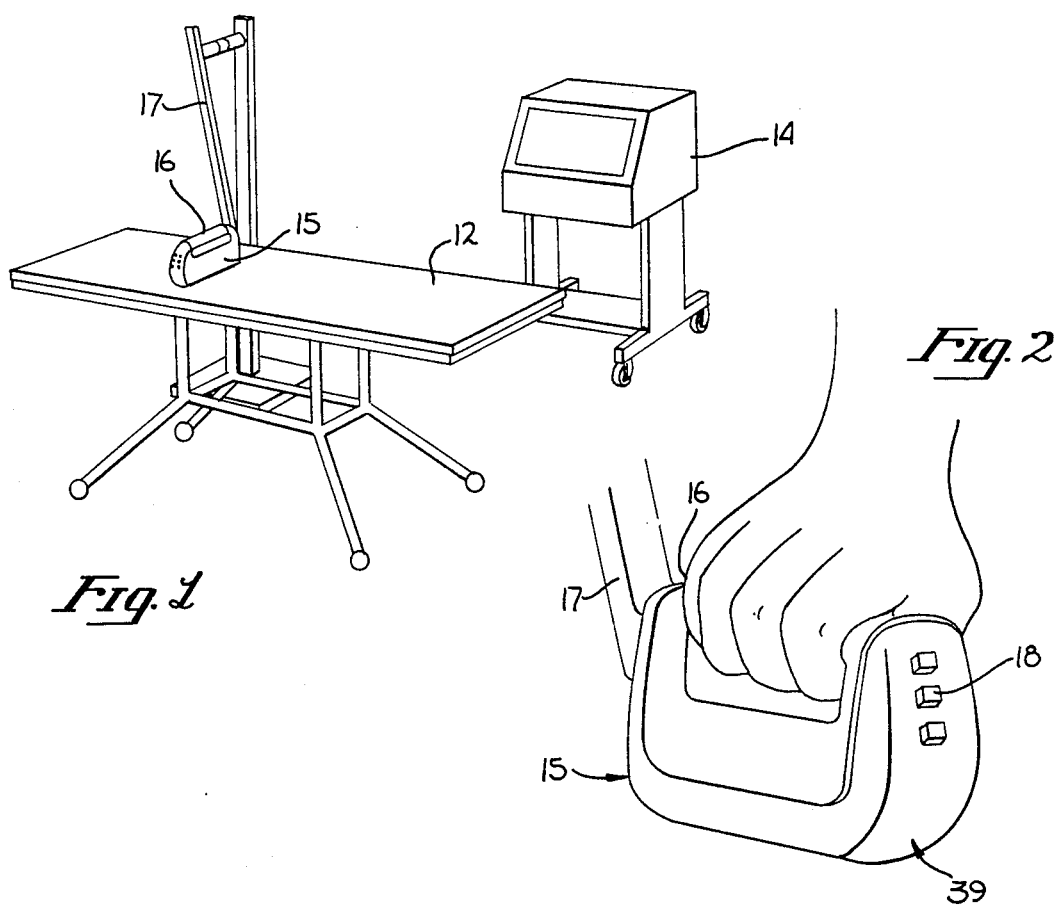
Fig. 1
Fig. 2
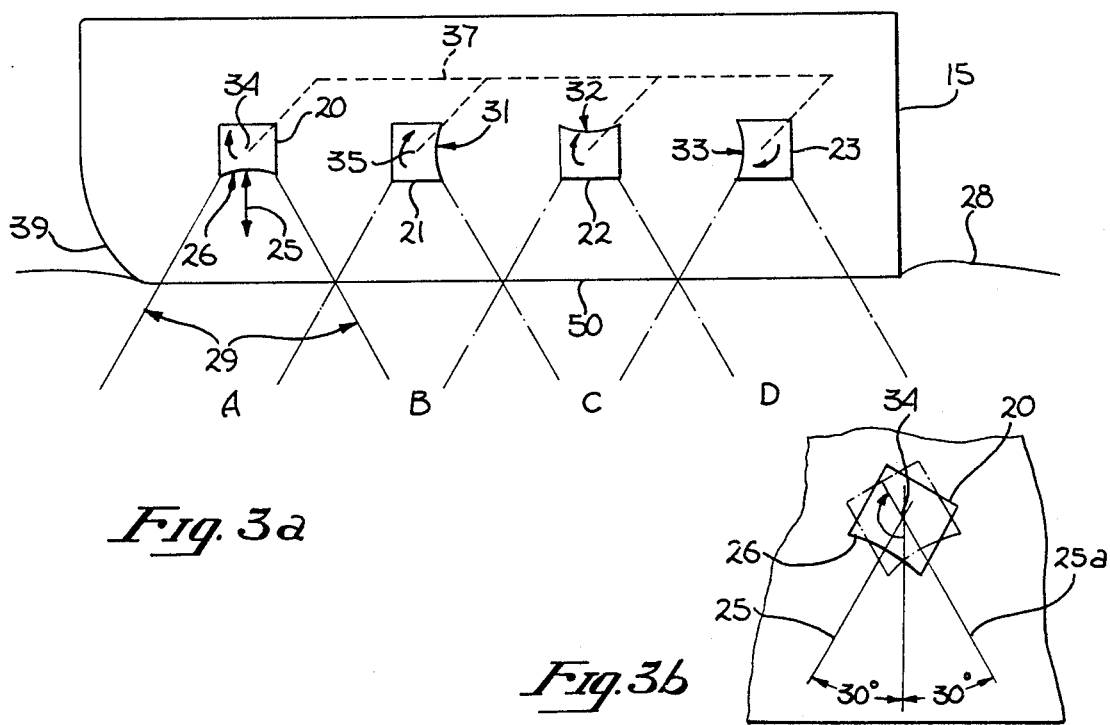
Fig. 3a
Fig. 3b

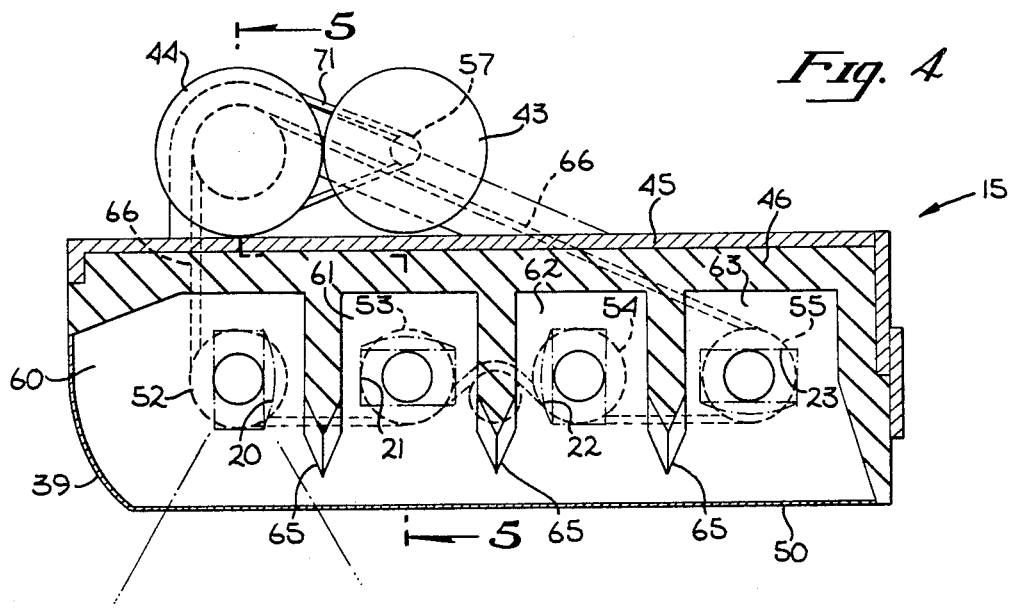
Fig. 4
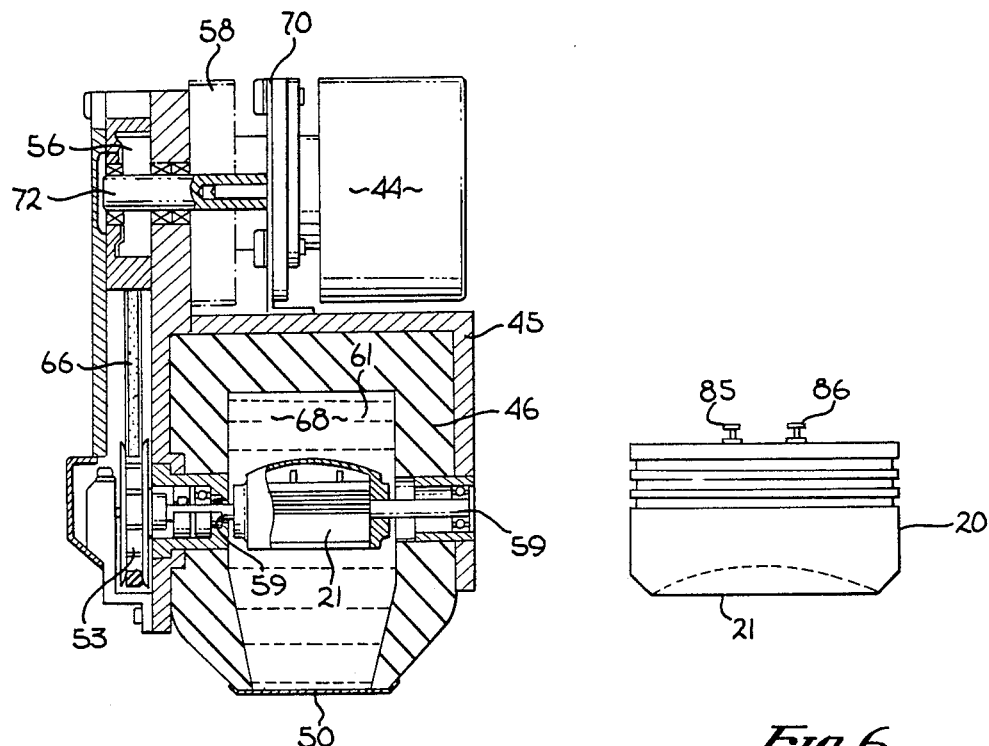
Fig 5
Fig. 6

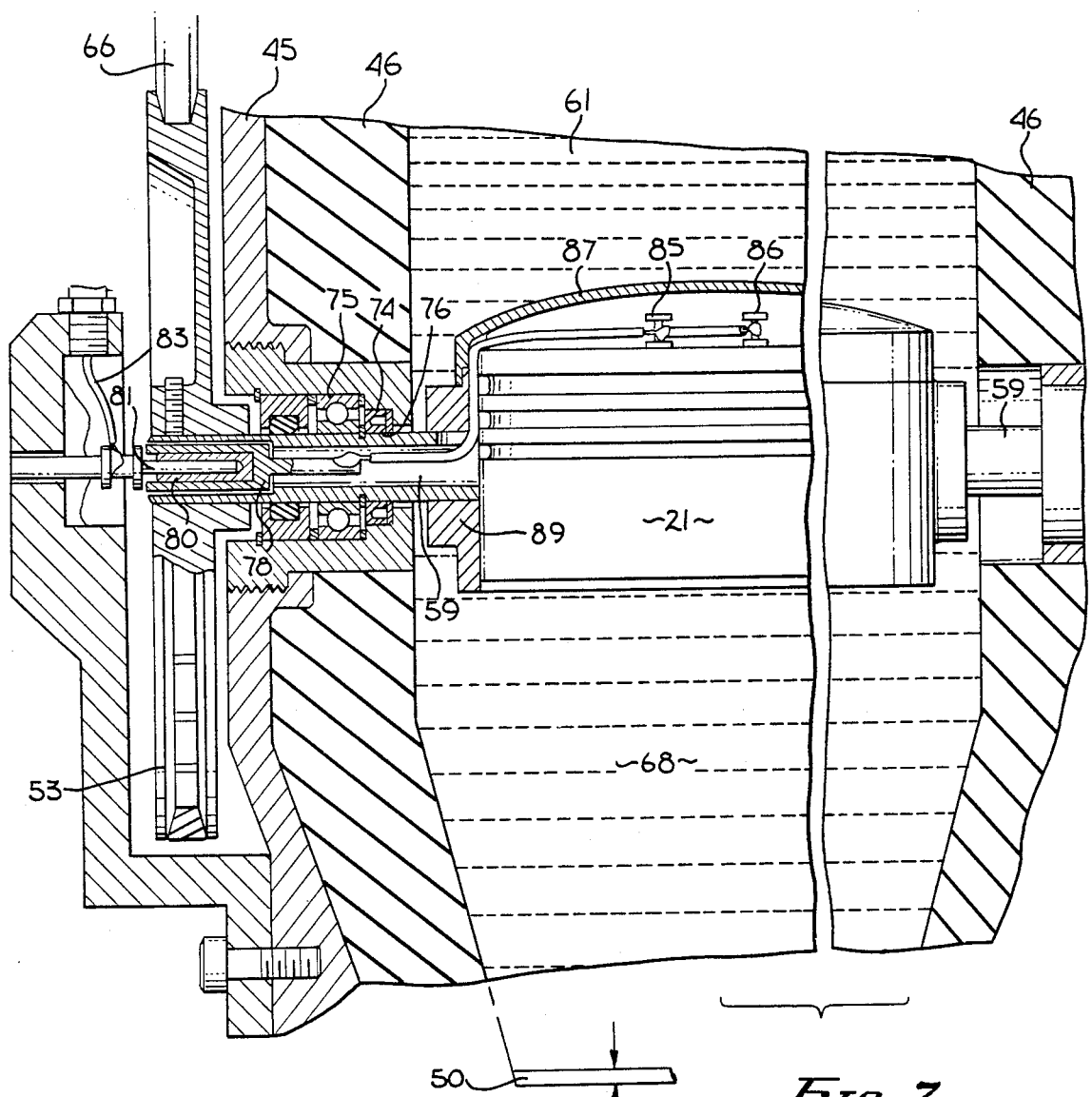
_Fig. 7_
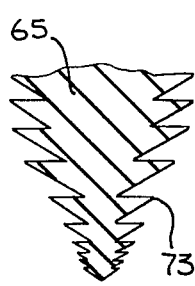
_Fig. 8_
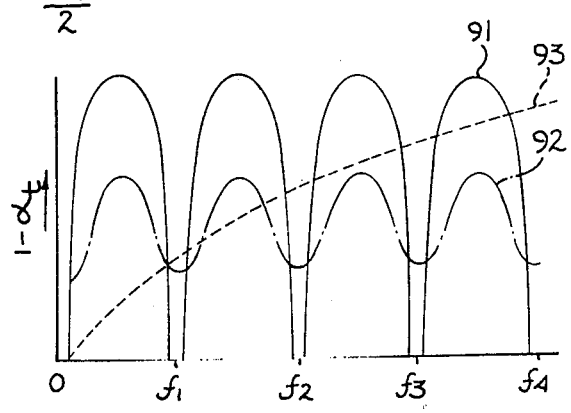
_Fig. 9_

ULTRASONIC IMAGING APPARATUS

BACKGROUND OF THE INVENTION

1. Field of the Invention

The invention relates to the field of ultrasonic imaging systems.

2. Prior Art

In recent years, more emphasis has been placed on the use of ultrasonics to provide anatomical images of soft tissue. This emphasis, to some extent, resulted from a public awareness of the dangers of X-rays, and also from the technical advances made in electronics. In the latter category, currently available integrated circuit memories, microprocessors, etc. have made possible the processing of signals that would not have been attempted a decade ago.

One of the more common imaging systems, commercially available today, employs a single transducer element which is manually moved over the area of interest to provide a compound B-display. The position of the transducer is followed through a relatively complex arrangement of arms and links to permit the painting of the B-display. This static imaging technique has the obvious disadvantage of not providing a real time display where movement of organs can be viewed. Moreover, even with a skilled operator, five to ten seconds are required for each picture, and through-put for such a system is generally one patient per hour.

A linear array of transducers is employed in other ultrasonic imaging systems. For example, 64 transducers are housed in a 15 centimeter long array in a commerical embodiment. These transducers are sequentially addressed to provide a B-display without movement of the array. The resulting single pass scans are of relatively poor quality since the smaller transducers required in the array have poorer characteristics than the larger transducers. These lower resolution images are used mainly in obstetrics where poorer images can be tolerated.

An imaging head with a single, larger transducer where the transducer is spaced-apart from the body is available. This imaging head is able to provide a wider field-of-view with a single transducer since the transducer is free to move. The transducer, which is housed in a bag of water brought into contact with the body, oscillates in an oscillating movement to provide the increased field-of-view. Placing the transducer away from the body to obtain this increased field-of-view introduces other problems. With the transducer spaced-apart from the body, reverberation between the transducer and the body may become significant. For example, if the transducer is spaced-apart from the body by a distance of three centimeters, the second reverberations sensed by the transducer may result in the appearance of an artifact at six centimeters below the skin. To solve this problem, the transducer is mounted a considerable distance from the body (e.g. 20 cm.). The resultant head is bulky and thus not easily handled. Another problem introduced by moving the transducer away from the body and having it in a water-filled bag (flexible membrane) is that the image is deteriorated because of refraction. The sound waves are disturbed as they enter and leave the body through the membrane. This cannot readily be corrected since the angle of incidence is unknown where a flexible bag, which conforms to the body in shape, is used.

More recently, an electronically steered ultrasonic array has been employed for ultrasonic imaging. Many transducers in the array are simultaneously addressed and each transducer is coupled through a variable delay line to provide an image. This array operates in a manner analagous to a phased array radar. However, these transducers are focused in one dimension only and often include undesirable side lobes.

As will be seen, the present invention provides an ultrasonic imaging head which has the advantages associated with the larger, high resolution transducers without the disadvantages inherent in the single transducer, static imaging devices. Those problems associated with the prior art heads where the transducers are spaced-apart from the body, are solved.

SUMMARY OF THE INVENTION

A data acquisition apparatus (head) for an ultrasonic imaging system is described. A plurality of transducers each for transmitting and receiving ultrasonic waves are mounted within a chamber which has a body contacting, semi-rigid membrane. The transducers are mounted for rotation in the chamber, each about an axis which is generally transverse to its axis of transmission. The transducers which are in a fixed angular displacement to one another are all driven at the same constant rate of rotation. The chamber in which the transducers rotate is filled with a liquid.

The acoustical impedance of the liquid, and its attenuation properties and the thickness of the membrane, are selected to enhance transmission into the body and to minimize the effects of reverberation. In the presently preferred embodiment, the acoustical impedance of the liquid is approximately equal to the acoustical impedance of the low density polyethylene membrane. The thickness of the membrane corresponds to a wavelength or half-wavelength at the transmission frequency.

BRIEF DESCRIPTION OF THE DRAWINGS

FIG. 1 is a general prospective view showing the entire imaging system, including the examination table and console.

FIG. 2 is a prospective view showing the data acquisition head of the present invention.

FIG. 3a is a schematic drawing showing the plurality of transducers and their relative orientation within the head of FIG. 2.

FIG. 3b is a schematic of a single transducer showing the angle during which it is activated.

FIG. 4 is a cross-sectional elevation view of the data acquisition head with the handle removed to reveal underlying structure.

FIG. 5 is a cross-sectional end view of the head of FIG. 4 taken generally through staggered section line 5—5 of FIG. 4.

FIG. 6 is an elevation view of a single transducer used in the presently preferred embodiment.

FIG. 7 is an exploded cross-sectional end view of the head which illustrates the manner in which the transducers are mounted within the liquid-filled chamber.

FIG. 8 is an exploded view of a portion of the baffling separating the transducers within the chamber taken generally through section line 8—8 of FIG. 4.

FIG. 9 is a graph used to describe the transmission characteristics of both prior art heads and the invented apparatus.

DETAILED DESCRIPTION OF THE INVENTION

Figure 10:
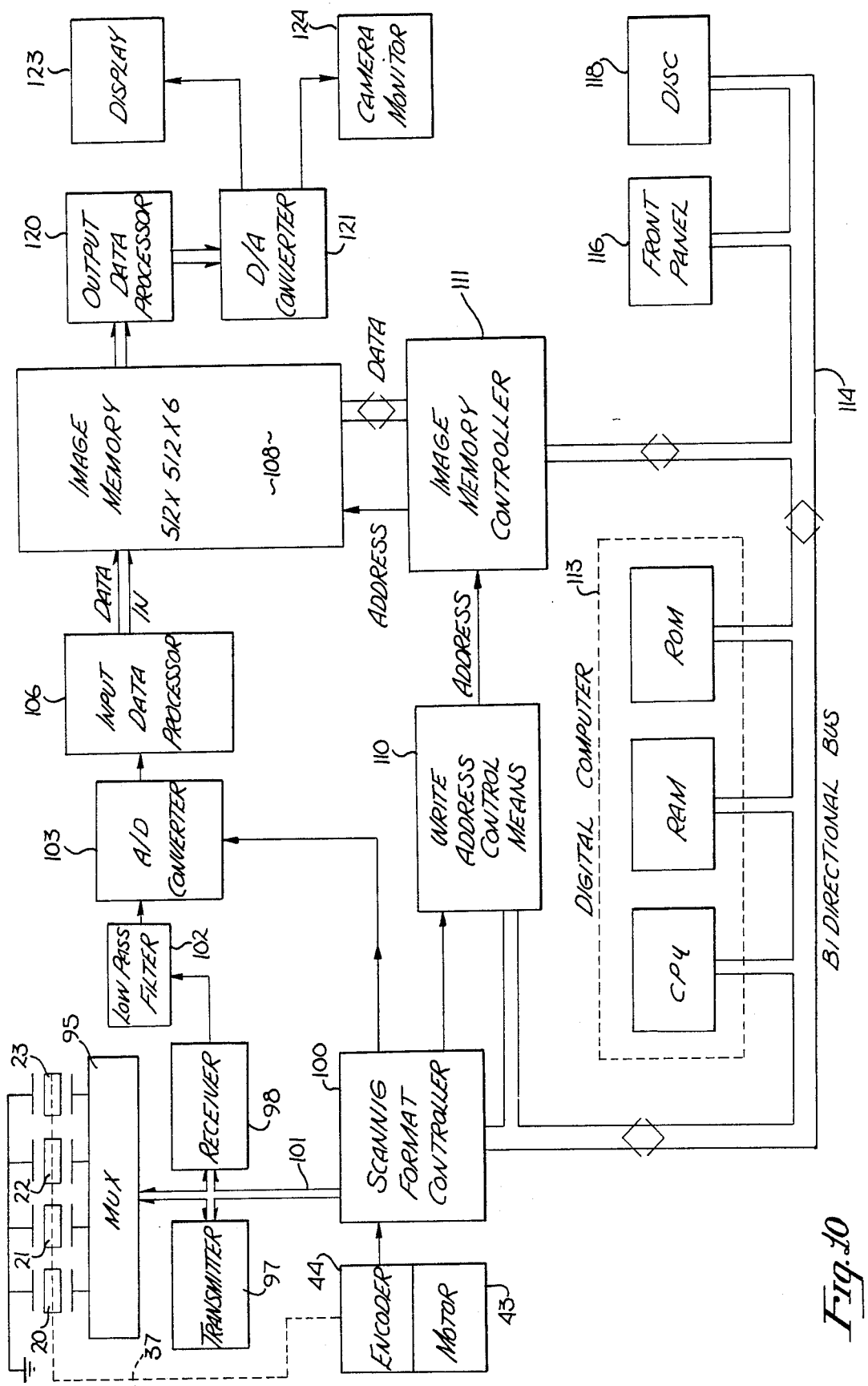
FIG. 10 is a general block diagram of the processing circuitry employed in conjunction with the invented head.

A data acquisition head for use in an ultrasonic imaging system is described. In the following description, numerous specific details, such as angles, frequencies, etc., are given to provide a thorough understanding of the invented apparatus. However, it will be obvious to one skilled in the art that the invention described in this application may be practiced without these specific details. In other instances, well-known components and structures have not been described in detail, in order not to obscure the present invention in unnecessary detail.

Referring first to FIG. 1, the overall imaging system includes the data acquisition head 15 mounted from a supporting arm 17. The head 15 is electrically coupled to a console 14. In typical operation, a patient is placed on the table 12 and the head 15 brought in contact with the area requiring examination. The operator controls the system from controls mounted on the console 14 and head 15 and views the images on a cathode ray tube or like display. As will be apparent from the description of the ultrasonic head 15, once the head is placed on the body, a B-display is obtained without movement of the head 15. The position and movement of the head 15 may be traced for global scans through the supporting arms and links, as is well-known.

Referring briefly to FIG. 2, the head 15 includes a grip 16 which allows the head to be easily manipulated. A plurality of buttons 18 are included on the head to allow selections of different modes of operation. The leading edge of the head 15 is curved, as will be described in greater detail, to allow examination, particularly under the last rib. As may be noted from FIG. 2 by the relative size of the head 15 and the hand holding it, the head is relatively small, making it easily manipulated.

As shown in the schematic drawing of FIG. 3a, the head 15, in its presently preferred embodiment, employs four identical ultrasonic transducers 20, 21, 22 and 23. Transducer 20 is also shown in FIG. 6. The transducers may be ordinary transducers, commonly employed for ultrasonic imaging for transmitting and receiving ultrasonic waves. In the presently preferred embodiment, the transducers have a nominal operating frequency of either 2.25 or 3.5 MHz and a focal length of 12 centimeters, with a sensitivity of 16 dB at this focal length. The transducers use an ordinary piezoelectric material and include a one-quarter wavelength epoxy front plate at their transmitting and receiving surface. This surface is shown as surfaces 26, 31, 32 and 33 for transducers 20, 21, 22 and 23, respectively. Each of the transducers transmits and receives ultrasonic waves in the direction of its transmission axis, such as the axis 25 shown for the transducer 20.

In the presently preferred embodiment, four transducers are mounted in-line within the head 15, spaced-apart from one another by a distance of approximately 32 mm. Each of the transducers is mounted for rotation about an axis which is transverse to its transmission axis. For example, the transducer 20 is mounted for rotation about axis 34, and similarly, transducer 21 rotates about the axis 35. The axis of transmission of each of the transducers are angularly spaced-apart from one another. In the presently preferred embodiment, with four transducers, the axis of transmission of each transducer are 90° apart. Thus, for the positions shown in FIG. 3a, the front face 26 of the transducer 20 is directed downward, the front face 31 of the transducer 31 is directed to the right, the front face 32 of transducer 22 is directed upward and the front face 33 of transducer 23 is directed to the left.

All the transducers are rotated at a constant speed about their axis of rotation as indicated by the dotted line 37. The relative angular separation of 90° between the transmission axes of the transducers remains constant. Thus, the axis of transmission, such as axis 25, for each transducer sequentially incident the membrane 50. For the described embodiment, the transducers rotate at a rate of either 75 or 100 rpm.

The transducers, for the described embodiment, are mounted approximately 2 centimeters from the membrane 50 such that their field-of-view, such as the field-of-view 29, intersect at about the skin line 28 as shown in FIG. 3a. As may be seen in FIG. 3b, each of the transducers are activated when its axis of transmission is at an angle of 30°, or less, normal to the membrane 50. For the transducer 20 shown in FIG. 3b, transmission (and reception) begins when the axis of transmission is in the position shown for axis 25a and ceases when the axis reaches the position of axis 25. Then for a period of time corresponding to 30° of rotation, no transmission occurs. Following this, transducer 21 will transmit and receive for 60° of rotation again followed by a period of time corresponding to 30° with no transmission. Then in a similar manner, transducers 22 and 23 will transmit and receive for their respective on-periods, followed by the activation of transducer 20, and so on.

As will be described in greater detail, the angular position of each of the transducers is always known. The ultrasonic returns accepted by each of the transducers during the period of time that it is activated is electrically limited so that, for example, transducer 20 only provides data for region A (FIG. 3a). Similarly, transducer 21 provides data for region B, transducer 22 for region C and transducer 23 for region D. In one mode of operation, by depressing one of the controls 18, the operator is able to expand the field-of-view for the transducer 20. Transducer 20 is activated over a larger angle than 60°. This is particularly useful when the curved section 39 is depressed under the last rib. In this mode of operation, most of the membrane 50 except at section 39 is not in contact with the body. Thus the head effectively operates as a single transducer head.

Referring to FIGS. 4 and 5, the transducers are mounted within the rubber chamber 46 which includes cavities 60, 61, 62 and 63 for receiving the transducers 20, 21, 22 and 23, respectively. Baffles 65 extend between the transducers 20 and 21, 21 and 22, and, 22 and 23, defining the cavities. The rubber chamber 46 is fabricated from a sound absorbing rubber which, in the presently preferred embodiment, has an acoustic impedance approximately equal to the impedance of the liquid 68 which fills the chamber. In this manner, ultrasound within the chamber more readily enters the baffles, and thus may be attenuated.

As shown in FIG. 8, each of the baffles 65 has serrated-like surfaces which further assist in dampening sound. The interior surfaces of the chamber 46 also has such serrated surfaces to provide a sound deadening chamber. The purpose of the rubber chamber 46 and the baffles 65 is to dampen reflected ultrasound within the chamber which greatly reduces reverberation.

The chamber 46 is mounted to a metal member 45 which provides rigidity to the rubber chamber and a mounting surface for a motor 43 and mechanical encoder 44. The motor 43 includes a pulley 57 which is coupled to a pulley 58 by a belt 71. As seen in FIG. 5, the pulley 58 is mounted on a shaft 72 which shaft includes a pulley 56 and the encoder 44.

Each of the transducers such as the transducer 21 shown in FIGS. 5 and 7 is mounted on a two-sectioned shaft 59. This shaft extends from one wall of the chamber 46 through the opposite wall where it terminates in a pulley and a "slip ring" assembly. A continuous belt extends from pulley 56 and into cooperative engagement with pulleys 52 and 53 (FIG. 4). The belt 66 passes over the idler wheel 64 and into cooperative engagement with the pulleys 54 and 55. The pulleys may use ribbed grooves for engaging a ribbed belt to assure that the four transducers and encoder remain directly coupled without slippage. Angular accuracies of approximately 1/10 of 1° are achieved. The electrical output of the encoder 44 provides a digital signal indicating the position of each of the transducers to within approximately 1/10 of 1°.

As shown in FIG. 7, the transducer 21 is mounted within a boss 89 which is coupled to the shafts 59. One lug 86 from the transducer is electrically coupled to the shaft to provide a ground. The other lug 85 is coupled through the center of the hollow shaft to a mercury-filled cup 78. A stationary contact 81 extends into the mercury. A lead 83 is connected to stationary contact 81 to allow electrical contact to be made through the "slip ring" assembly to the lug 85. Note that rotating transformers or other means may be employed in place of the illustrated "slip ring" assembly.

The shaft 59 is supported for rotation by a bearing 75 at the "slip ring" assembly. The liquid 68 is retained in the chamber at the shaft 59 by the dynamic seal 74. In the presently preferred embodiment, the shaft 59 at the area 76 includes spiral grooves which tend to pump the liquid back into the chamber.

The body contacting surface of the head 15 consists of a substantially rigid membrane 50. As shown in FIG. 5, the membrane 50 sealingly engages the lower surfaces of the chamber 46 to define a volume in which the fluid 68 is retained. As is apparent, the transducers rotate within the fluid. As shown in FIG. 3a, even though the membrane 50 is semi-rigid, intimate contact between the membrane and the skin 28 is easily made because of the generally pliable nature of the body.

There are a number of advantages to using a relatively thick (e.g., 40 mils) semi-rigid membrane. Prior art approaches have lead away from such membranes in favor of very thin membranes (e.g., 1 mil) for acoustic consideration, which will be described in conjunction with FIG. 9. The thicker membranes are easier to seal, thus making fluid retention in the chamber less a problem. These membranes are obviously more durable and less likely to be damaged during use.

Another advantage to a semi-rigid or rigid membrane is that the angle between the membrane and transducer frame remains fixed. Therefore, the angle of incidence of the sound waves at the membrane is always known (assuming the transducer's position is known). Note that this is not the case where a transducer is housed in a water-filled bag which conforms to the body shape. Since the angle of incidence is always known, compensation for refraction may be provided, as it is in the presently discussed imaging system. A look-up table in the form of a read-only memory provides a conversion between the apparent angle of an echo and the actual angle of the echo. This correction is obviously greater when the axis of transmission is at an angle of 30° with respect to the normal and decreases to zero when the axis of transmission is perpendicular to the membrane.

The equation for the transmission coefficient at a given frequency, f, for transmission through the membrane 50 may be written as:

$$\alpha_t = \frac{4Z_\beta Z_L}{(Z_\beta + Z_L)^2 \cos^2 kl + \left(Z_m + \frac{Z_\beta Z_L}{Z_m}\right)^2 \sin^2 kl}$$

where $Z_B$ is the acoustic impedance of the body, $Z_L$ the acoustic impedance of the liquid, $Z_M$ the acoustic impedance of the membrane, $k=2\pi f/V_M$ and $l=$ thickness of the membrane. ($V_M=$ velocity of sound in the membrane.) A plot of $1-\alpha_t$ (reflection coefficient) versus frequency results in the curve generally shown by curve 91, FIG. 9. It is apparent from an examination of this curve and the above equation that the lower reflection occurs when the thickness of the membrane is equal to $n(\lambda/2)$ ($kl=n\pi$). However, the curve 91 shown that the reflection characteristics at other than the center frequencies (e.g. $f_1$, $f_2$, etc.) are very poor. Since the transducer typically provides a band of frequencies, many of these frequencies will not be transmitted through the membrane, but reflected back into the chamber. Note the sharp characteristics shown by the curve 91 for frequencies above and below the center frequencies. For this reason, it has generally been assumed that a very thin membrane provides the lowest reflection characteristics. These characteristics are shown by the curve 93 which, for example, could represent a thin (e.g. 1 mil) flexible membrane.

By performing a broadband analysis on the above equation and by considering various membrane materials, it has been concluded that a thick membrane may be put to beneficial use by properly matching $Z_M$ and $Z_L$. The reflection characteristics for the selected combinations are shown generally by curve 92. The transmission is more constant over a broadband. The average reflection coefficient is lower for this combination than, for example, curve 91.

In the presently preferred embodiment, polyethylene, particularly a low-density polyethylene, has been selected as the membrane material. The thickness of the material corresponds to a half wavelength or a full wavelength at the center frequency of the transducer. In one embodiment, the membrane has a thickness of 40 mils and is, therefore, substantially rigid. The $Z_M$ for this low-density polyethylene ranges approximately between 1.8 and 2.0. It has been determined that the acoustic impedance of the liquid 68 should be approximately equal to that of the membrane. An emulsion and a mixture have been found to meet these requirements with non-toxic fluids.

A mixture comprising by volume of 48% of a derivative of polyethylene oxide and propylene oxide, 19% glycerine and 28% water, plus 5% of an anti-foaming agent (SURFONIC N-95), provides the desired acoustic impedance of approximately 1.7–1.8. Also this mixture provides sufficient attenuation to reduce reverberation for 2.25 MHz. At 3.5 MHz. a mixture by volume of 40% of a derivative of polyethylene oxide and propylene oxide, 19% glycerine, 36% water and 5% Surfonic (N-95) is employed. This latter mixture has approximately the same impedance, however, provides the correct attenuation for this higher frequency.

An emulsion consisting of 33% water, 33% glycerine and 33% castor oil with a "Tweening" agent has also been found to provide the required acoustic impedance and attenuation.

By employing the thick membrane of polyethylene along with a fluid having an acoustic impedance approximately equal to that of the membrane, optimized transmission into the body is obtained. Because of this transmission, the attenuation of the ultrasound by the liquid, and the sound-deadening chamber, reverberation is not a problem. For this reason, the transducers need not be mounted as far distant from the body as required with other heads. (The plurality of transducers, such as four in the presently preferred embodiment, provide the increased field-of-view.)

The signals from the four transducers may be processed in any one of a number of well-known ways for display on a cathode-ray tube or for recording. In FIG. 10, a general block diagram of the processing employed with the head 15 is shown.

The four transducers 20, 21, 22 and 23 are again shown in FIG. 10. One terminal from each of these transducers is coupled to a multiplexer 95. The other terminal is coupled to ground. The multiplexer 95 allows the transmitter 97 and receiver 98 to be sequentially coupled to each of the four transducers as they are each activated in the manner described above. The transmitter 97 provides the ultrasonic pulses of 2.25 or 3.5 MHz. These pulses are typically three hundred volts and are directly coupled to the transducers which have a nominal impedance of approximately 50 ohms. The returns sensed by these transducers are coupled by the lines 101 to the receiver 98. These returns typically vary in range between 100 millivolts and 10 microvolts. The receiver 98 also includes a time-gain control means which varies the gain of the receiver to provide additional gain for the later received returns, as is commonly done.

The motor 43 and encoder 44 are shown coupled to the transducers for driving the transducers at a constant speed as depicted by the dotted line 37. The encoder 44 which provides the position information for the transducers is coupled to a scanning format controller 100.

The output of the receiver 98 is passed through a lowpass filter 102 and then to an analog-to-digital converter 103. In the converter 103, the signals are sampled and converted to 8-bit digital words for the presently preferred embodiment. Each of these words is coupled to an input processor 106. In the input processor, a plurality of known functions are performed, including data weighting, filtering, aperture correction and a logarithmic compression. The output of the processor 106 are 6-bit words which are coupled to the random-access memory 108 identified as the "Image Memory". This memory, for the presently preferred embodiment, is a 512×512×6 memory and provides 6-bit pixels for displaying the images. The output of the memory is coupled to an output data processor 120 which performs a gray scale correction. The processor 120 is coupled to a digital-to-analog converter 121 to convert the digital signals into appropriate video signals for a display 123 or for a camera monitor 124.

The scanning format controller 100 controls the transmitter 97 and the receiver 98. As mentioned, the controller knows the position of the transducers from the signals supplied by the encoder 44. The controller, in conjunction with the write address control means 110, essentially draws vectors in digital space which correspond to the images tracked by the transducers. These vectors are employed to provide addresses to the image memory controller 111. Thus, as the transducers rotate and receive signals which are processed for storage in the memory 108, addresses are simultaneously generated to allow the received signals to be stored in the proper location within the memory. Also the write address control means 100 provides the refraction correction previously mentioned.

In the presently preferred embodiment, the digital computer 113 comprises an LSI-11-2 microprocessor, a 4K RAM and an 8K control memory (ROM). The computer 113 communicates through a bidirectional data bus 114 and with various units in the system such as the controllers 100 and 111, write address control means 110, front panel 116 and a disc recorder 118. The computer 113 is used to perform a plurality of housekeeping functions and to perform arithmetic functions including averaging of data stored within the memory 108 to enable a compound scan.

Thus, an imaging head for an ultrasonic imaging system has been described. The head includes a plurality of transducers which are rotated at a constant speed at a fixed angular displacement to one another. The transducers are submerged in a liquid which has an acoustic impedance approximately equal to the impedance of the semirigid membrane which serves to retain the liquid within the head. This membrane, in the presently preferred embodiment, comprises polyethylene and is one-half wavelength or a wavelength thick. The imaging head provides a high resolution, real time image.

What is claimed is:

1. An image acquisition apparatus for an ultrasonic imaging system comprising:
    a housing defining a chamber, said housing including a body contacting membrane;
    a plurality of transducers, each for transmitting and receiving ultrasonic sound, each of said transducers having an axis of rotation;
    mounting means coupled to said housing for mounting each of said transducers for rotation in said chamber about its said axis of rotation, such that said axes of rotation are spaced-apart and parallel to one another;
    driving means coupled to said mounting means for rotating said transducers at a constant rate of continuous uni-directional rotation about their respective said axes of rotation, and
    a liquid disposed within said cavity,
    whereby as said transducers rotate, a high resolution, real time image over a large field-of-view is obtained.

2. The apparatus defined by claim 1 wherein each of said transducers has a transmission axis and said transmission axes of said transducers are angularly displaced from one another by a fixed, predetermined angle.

3. The apparatus defined by claim 2 wherein said chamber includes baffles disposed between said transducers.

4. An image acquisition apparatus for an ultrasonic imaging system comprising:
    a housing defining a chamber, said housing including a body contacting membrane;

a plurality of transducers, each for transmitting and receiving ultrasonic sound, each of said transducers having a transmission axis for said transmitting and said receiving ultrasonic sound;

mounting means coupled to said housing for mounting each of said transducers for rotation in said chamber, each of said transducers being rotated about a separate axis of rotation, each of said axes of rotation being perpendicular to, and intersecting said transmission axis of its respective transducer;

driving means coupled to said mounting means for rotating each of said transducers about its said axis of rotation at a constant rate of continuous uni-directional rotation such that each of said axes of transmission crosses said membrane; and a liquid disposed within said cavity, whereby as said transducers rotate, a high resolution, real time image over a large field-of-view is obtained.

5. The apparatus defined by claim 4 wherein said transmission axes of said transducers are angularly displaced from one another by a fixed, predetermined angle.

6. A hand-holdable, ultrasound imaging head comprising:

a hand-holdable housing defining a chamber, said housing including a body contacting member;

a plurality of transducers, each for transmitting and receiving ultrasound along a beam axis;

each of said transducers mounted within said housing for rotation above a different area of said body contacting member, driving means coupled to said transducers for synchronously rotating each of said transducers completely about its axis of rotation at a constant rate of continuous uni-directional rotation such that each of said beam axes remain angularly spaced-apart from one another;

whereby, as said transducers rotate, a high resolution, real time image over a large field-of-view is obtained.

* * * * *